United States Statutory Invention Registration [19]

[11] Reg. Number: H754

Wallace et al. [43] Published: Mar. 6, 1990

[54] ARLOXY P-PHENYLENE DIAMINES

[75] Inventors: J. Shield Wallace, Albuquerque, N. Mex.; Fred E. Arnold, Centerville, Ohio

[73] Assignee: The United States of America as represented by the Secretary of the Air Force, Washington, D.C.

[21] Appl. No.: 249,547

[22] Filed: Sep. 26, 1988

[51] Int. Cl.[4] ..... C07C 93/14
[52] U.S. Cl. ..... 564/430
[58] Field of Search ..... 564/430

[56] References Cited

U.S. PATENT DOCUMENTS

| | | | |
|---|---|---|---|
| 1,574,337 | 2/1926 | Bogert | 564/430 |
| 3,122,575 | 2/1964 | Peterson et al. | 564/430 |
| 3,506,767 | 4/1970 | Frick et al. | 564/430 |

OTHER PUBLICATIONS

*Chemical Abstract* vol. 107(2) #176,568h, Wallace et al.

*Primary Examiner*—John F. Terapane
*Assistant Examiner*—Chhaya Sayala
*Attorney, Agent, or Firm*—Donald J. Singer; Charles E. Bricker

[57] ABSTRACT

There are provided substituted p-phenylene diamines of the formula

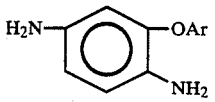

wherein Ar is phenyl or phenoxyphenyl.

2 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ARLOXY P-PHENYLENE DIAMINES

The invention described herein may be manufactured and used by or for the Government of the United States for all governmental purposes without the payment of any royalty.

BACKGROUND OF THE INVENTION

This invention relates to substituted P-phenylene diamines.

Considerable research effort has been directed toward the synthesis of rigid rod polymers for their unique ordering properties that provide extremely high modulus/high strength films and fibers. One class of materials of particular interest is the aromatic heterocyclic bisbenzazole polymers. These polymers exhibit excellent thermal and thermooxidative stabilities. Another class of materials having comparable high temperature properties is the aromatic polyimides. The polyimides are attractive, not only for their high temperature properties, but also because of the low cost of the diamine and dianhydride monomers used in their synthesis.

An aromatic polymide with the desired para-ordered geometry and be prepared from pyromellitic dianhydride (PMDA) and p-phenylene-diamine. High molecular weight polyamic acid has been prepared in dimethylacetamide (DMAC) using these monomers; however, thermal or chemical cyclodehydration leads to an insoluble, infusible material. Fabrication of this material is normally carried out via the DMAC-soluble polyamic acid which produces two units of water per repeat unit during high temperature thermal cyclodehydration to the imide structure. The water produced by this process limits the utility of this material, particularly in the fabrication of thick components.

It is known that certain polyisoimides can be used to form the corresponding polyimides by thermal curing. Such polyisomides may be prepared by reacting a carboxylic acid dianhydride with a tetravalent aromatic diamine to produce a polyamic acid, and treating the resulting polyamic acid with a dehydrating agent to produce the corresponding polyisoimide. The polyisoimide to polyimide route is attractive from the standpoint that in the course of thermal curing no water vapor is released which could cause voids or defects in thick components. In general, the soluble polyisoimides prepared from aromatic diamines disclosed in the prior art are not linear, i.e., that portion of the polymer backbone contributed by the diamine is either not para-oriented with respect to the amino groups, or contains a non-linear constituent.

As mentioned previously, the aromatic polyimide prepared from pyromellitic dianhydride and p-phenylene diamine has the desired para-ordered geometry. This polymer has attractive high temperature properties and low cost. Unfortunately, when prepared via the soluble polymic acid route, the utility of the polymer is limited because of the water produced in the thermal cyclodehydration step.

We attempted to prepare a polyimide from pyromellitic dianhydride and p-phenylene diamine via the polyisoimide to polyimide route. We found that the polyisoimide prepared from these monomers was insoluble in all the solvents tested.

Accordingly it is an object of the present invention to provide p-phenylene diamine compounds which, when reacted with pyromellitic dianhydride, provide soluble polyisoimides.

Object objects of the invention will be apparent to those skilled in the art.

DESCRIPTION OF THE INVENTION

In accordance with the present invention, there are provided substituted p-phenylene diamines of the formula

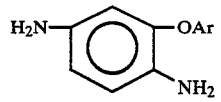

I wherein Ar is phenyl or phenoxyphenyl.

The compounds of this invention are prepared as shown by the following reactions:

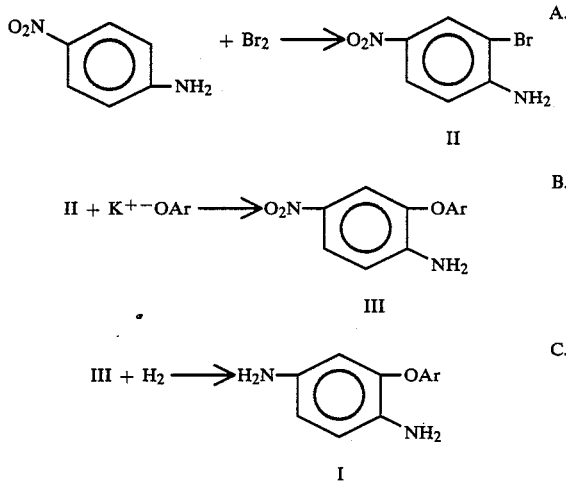

In reaction A. above, p-nitroaniline is brominated to provide 2-bromo-4-nitroaniline. The reaction is carried out in a suitable reaction medium, such as glacial acetic acid, at a temperature in the range of about 0° C. to 30° C.

In the next step of the synthesis, as shown by reaction B, the bromine is replaced by an aryloxy group. The 2-bromo-4-nitroaniline prepared above is reacted with the potassium or other alkali metal salt of phenol or a phenoxyphenol, such as 3-phenoxyphenol, in the presence of a suitable catalytic agent, such as copper-bronze to provide a 2 -aryloxy-4-nitroaniline. The reaction is carried out at an elevated temperature of abut 100° C. to 150° C. for about 4 to 24 hours.

In the final step of the synthesis, as shown by reaction C, the 2-aryloxy-4-nitroaniline is hydrogenated, using a suitable hydronegation apparatus to provide the desired aryloxy-p-phenylene diamine.

The substituted p-phenylene diamines of the present invention are useful in preparing soluble isoimide polymers which can be thermally converted to rod-like, para-ordered imide polymers.

The following examples illustrate the invention:

EXAMPLE I

2-bromo-4-nitroaniline 100 g (0.724 mol) of p-nitroaniline was slowly added to 1550 ml of glacial acetic acid at 40° C. After cooling the solution to 20° C., 37.4 ml (116.65 g, 0.730 mol) of bromine was added dropwise over a period of one h, after which the solution was allowed to stir an additional 45 min. at 20° C. The precipitate which formed during the reaction was collected by suction filtration and stirred with 2500 ml of 10% aqueous sodium bisulfite for 16 h; collected again by suction filtration and washed with 2500 ml of water. The solid was air-dried for 24 h. The crude material (139 g) was recrystallized twice from 65% methanol to yield 103 g (65.6%) of a yellow crystalline solid which melted at 101°-102° C.; IR (KBr) 3500, 3400, 1125 $cm^{-1}$ ($NH_2$); 1500, 1325 ($NO_2$).

Anal. Calcd. for $C_6H_5N_2O_2Br$: C,33.18; H, 2.30; N, 12.90. Found: C, 33.26; H, 2.28; N, 12.92.

EXAMPLE II

2-Phenoxy-4-Nitroaniline

A solution of potassium carbonate (9.66 g, 0.07 mol) and phenol (12.99 g, 0.14 mol) was formed with heating (120° C., under nitrogen in a three-necked, 50 ml round-bottom flask equipped with reflux condenser, magnetic stir bar, and a gas inlet/outlet adapter. Next, copper-bronze (0.5 g) was added with stirring and the mixture temperature maintained. While stirring, 2-bromo-4-nitroaniline (5.0 g, 0.025 mol) was added in two equal portions and the reaction temperature raised to 135° C., and maintained overnight. The dark reaction mixture, while still hot, was poured into 600 ml of 1N aqueous potassium hydroxide and stirred for 1 h. From this procedure a dark brown precipitate was collected on diatomaceous filter aid by suction filtration. The filter aid and precipitate mixture were extracted with 150 ml of methylene chloride and dried under vacuum. The dark gray solid (~4.2 g) was chromatographed on a quartz column filled with activated silica gel (400 g). The second band was eluted with methylene chloride/hezanes (1/1) to yield 3.93 g of a yellow-orange solid which was recrystallized from ethanol/water (4.1) to yield 3.61 g (58.1%) of a light yellow crystalline solid: mp 116°-117° C.; IR (KBr) 3500, 3360 $cm^{-1}$ ($NH_2$), 1490, 1290 $cm^{-1}$ (NO), 1225 $cm^{-1}$ (ArOAr); $^{H}$NM R 6.71-8.15 (m, aromatic, 8 H), 4.75 (s amino, 2 H).

Anal. Calcd. for $C_{12}H_{10}N_2O_3$: C 62.60; H, 4.38; N, 12.17. Found: C, 62.64; H, 4.38; N, 11.78.

2-phenoxy-1,4-diaminobenzene dihydrochloride

In a 500 ml Paar hydrogenator flask, equipped with mechanical agitator and high pressure hydrogen inlet, were added 2-phenoxy-4-nitroaniline (3.5 g, 15.2 mmOl). 10% palladium on charcoal (0.3 g), and 75 ml of ethanol which had been previously saturated with hydrogen chloride gas. The flask was pressurized to 50 psig and agitated 16 h. The resulting clear colorless solution was pressure filtered with nitrogen through diatomaceous filter aid which had been previously washed with hydrogen chloride saturated ethanol to remove the catalyst. The collected filtrate was saturated with hydrogen chloride gas and 50 ml of anhydrous diethyl ether added (causing a slight cloudiness). Upon cooling overnight (0° C.) a white precipitate formed, was collected by nitrogen pressure filtration, and dried under vacuum at 60° C., over phosphorus pentoxide for 48 h to yield 3.56 g (85.78%) of a white solid: mp decomposed above 120° C.; IR (KBr) 1620 $cm^{-1}$ ($NH_2$), 1205 $cm^{-1}$ (ArOAr).

Anal. Calcd. for $C_{12}H_{14}N_2Cl_2O$: C, 52.76; H, 5.17; N, 10.26 Cl, 25.96, Found: C, 49.55; H, 4.71; N, 9.35; Cl, 29.12.

EXAMPLE III

2-(3-phenoxyphenyleneoxy)-4-nitroaniline

A solution of potassium carbonate (7.74 g. 0.06 mol) and 3-phenoxyphenol (20.86 g, 0.112 mol) was formed with heating 110° C.) under nitrogen in a three-necked, 50 ml round-bottom flask equipped with reflux condenser, magnetic stir bar and a gas inlet/outlet adapter. Copper-bronze (0.5 g) was added with stirring. After mixing well, 2-bromo-4-nitroaniline (6.0 g 0.028 mol) was added in two equal portions and the reaction temperature raised to 135° C. and maintained for 5 h. The dark reaction mixture, while still hot, was poured into 700 ml of 1N aqueous potassium hydroxide and stirred for 1 h. From this mixture a fine, dark brown precipitate was collected on diatomaceous filter aid by suction filtration. The filter aid and precipitate mixture were extracted with 200 ml of methylene chloride, dried (magnesium sulfate), concentrated (rotary evaporator), and dried under vacuum. The dark red-brown solid (~7.33 g) was chromatographed on a quartz column filled with activated silica gel (500 g). The first major band (orange) was eluted with methylene chloride/hezane (2.1) to yield 6.9 (6.11?)g of an orange-yellow crystalline solid which was recrystallized from isopropanol/water (4/1) to yield 6.61 g (73.2%) of bright yellow plate-like crystals: mp 121°-122° C.; IR (KBr) 3500, 3380 $cm^{-1}$ ($NH_2$), 1500, 1295 $cm^{-1}$ ($NO_2$), 1210 $cm^{-1}$(ArOAr); $^{1}$H NMR 7.80-8.15 (m, aromatic, 2H), 6.60-7.55 (m, aromatic, 10 H), 4.65 (s, amino, 2H).

Anal. Calcd. for $C_{18}H_{14}N_2O_3$: C, 67.07, H, 4.37; N, 8.69. Found: C, 67.10, H, 4.49; N, 8.91.

2-(3-phenoxyphenyleneoxy)-1,4-diaminobenzene dihydrochloride

In a 500 ml Paar hydrogenator flask, equipped with mechanical agitator and high pressure hydrogen inlet, were added 2-(3-phenoxyphenyleneoxy)-4-nitroaniline (4.00 g, 12.4 mol), 10% palladium on charcoal (0.4 g), and 150 ml of ethanol which had been previously saturated with hydrogen chloride gas. The flask was pressurized to 50 psig and agitated 18 h. The resulting clear colorless solution was pressure filtered with nitrogen through diatomaceous filter aid, which had been previously washed with hydrogen chloride saturated ethanol to remove the catalyst. The collected filtrate was saturated with hydrogen chloride gas and 100 ml of anhydrous diethyl ether added (causing a slight cloudiness). Upon cooling overnight (O.C.) a white precipitate formed and was collected by nitrogen pressure filtration and dried under vacuum at 60° C. over phosphorus pentoxide for 24 h to yield 3.67 g, (81%) of a white solid: mp decomposed above 140° C.; IR (KBr) 1627 $cm^{-1}$ ($NH_2$), 1215 $cm^{-1}$ (ArOAr).

Anal. Calcd. for $C_{18}H_{18}N_2O_2Cl_2$: C, 59.19; H, 4.97; N, 7.17; Cl, 19.41. Found: C. 54.73; H, 4.50; N, 7.15; Cl, 24.16.

Various modifications may be made without departing from the spirit of the invention or the scope of the appended claims.

We claim:

1. 2-phenoxy-1,4-diaminobenzene.
2. 2-(3-phenoxyphenyleneoxy)-1,4-diaminobenzene.

* * * * *